United States Patent
McGowan et al.

(10) Patent No.: US 9,045,463 B2
(45) Date of Patent: Jun. 2, 2015

(54) PHENYL ETHYNYL DERIVATIVES AS HEPATITIS C VIRUS INHIBITORS

(75) Inventors: David McGowan, Brussels (BE); Samuel Dominique Demin, Mechelen (BE); Stefaan Julien Last, Lint (BE); Koen Vandyck, Paal-Beringen (BE); Pierre Jean-Marie Bernard Raboisson, Rosieres (BE)

(73) Assignee: Janssen R&D Ireland, Little Island, Co. Cork (IE)

( * ) Notice: Subject to any disclaimer, the term of this patent is extended or adjusted under 35 U.S.C. 154(b) by 421 days.

(21) Appl. No.: 13/389,269

(22) PCT Filed: Aug. 6, 2010

(86) PCT No.: PCT/EP2010/061493
§ 371 (c)(1),
(2), (4) Date: Feb. 7, 2012

(87) PCT Pub. No.: WO2011/015657
PCT Pub. Date: Feb. 10, 2011

(65) Prior Publication Data
US 2012/0136027 A1    May 31, 2012

(30) Foreign Application Priority Data
Aug. 7, 2009   (EP) .................................. 09167438

(51) Int. Cl.
*A61K 31/4178*   (2006.01)
*C07D 403/14*   (2006.01)
*C07D 403/04*   (2006.01)
*C07D 405/14*   (2006.01)
*C07D 413/14*   (2006.01)

(52) U.S. Cl.
CPC ............ *C07D 403/14* (2013.01); *C07D 403/04* (2013.01); *C07D 405/14* (2013.01); *C07D 413/14* (2013.01)

(58) Field of Classification Search
CPC .................... A61K 31/4178; C07D 403/147
USPC ......... 548/311.1, 312.4, 312.7; 514/385, 396, 514/397
See application file for complete search history.

(56) References Cited

U.S. PATENT DOCUMENTS 8,088,368 B2 *  1/2012  Guo et al. .................... 424/85.4
8,273,341 B2 *  9/2012  Guo et al. .................... 424/85.4

FOREIGN PATENT DOCUMENTS

| WO | WO2006133326 A1 | 12/2006 |
| WO | WO2008021927 A2 | 2/2008 |
| WO | WO2008021928 A2 | 2/2008 |
| WO | WO2008048589 A2 | 4/2008 |
| WO | WO2008/125599 A1 | 10/2008 |
| WO | WO2010065668 A1 | 6/2010 |

OTHER PUBLICATIONS

Krieger, et al., Enhancement of Hepatitis C Virus RNA Replication by Cell Culture, Journal of Virology, May 1, 2001, 75-10, 4614-1624.
Lohmann, et al., Replication of Subgenomic Hepatitis C Virus RNAs in a Hepatoma Cell Line, Science, 1999, vol. 285, pp. 110-113.
European Search Report, for EP Application No. 09167438.2-2117 dated Nov. 4, 2009.

* cited by examiner

*Primary Examiner* — Golam M Shameem

(57) ABSTRACT

Inhibitors of HCV replication of formula I

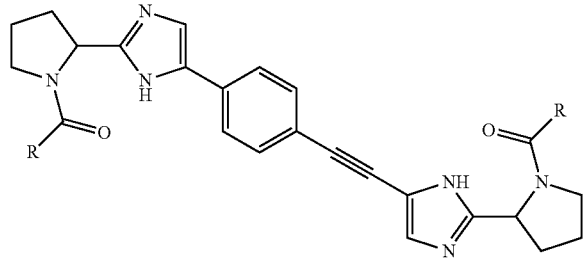

including stereochemically isomeric forms, and salts, hydrates, solvates thereof, wherein R and R* have the meaning defined in the claims.
The present invention also relates to processes for preparing said compounds, pharmaceutical compositions containing them and their use, alone or in combination with other HCV inhibitors, in the treatment or prophylaxis of HCV.

9 Claims, No Drawings

PHENYL ETHYNYL DERIVATIVES AS HEPATITIS C VIRUS INHIBITORS

This application is a national stage application of PCT/EP2010/061493, filed Aug. 6, 2010, which claims priority benefit of Application No. EP 09167438.2 filed Aug. 7, 2009. The complete disclosures of the aforementioned related patent applications are hereby incorporated herein by reference for all purposes.

TECHNICAL FIELD

This invention relates to phenylethynyl derivatives, which are inhibitors of the hepatitis C virus (HCV) and their use, alone or in combination with other HCV inhibitors, in the treatment or prophylaxis of HCV.

BACKGROUND ART

HCV is a single stranded, positive-sense RNA virus belonging to the Flaviviridae family of viruses in the hepacivirus genus. The viral genome translates into a single open reading frame that encodes for multiple structural and non-structural proteins.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and hepatocellular carcinoma, making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5A protein of HCV is located downstream of the NS4B protein and upstream of the NS5B protein. Upon post-translational cleavage by the viral serine protease NS3/4A, the NS5A matures into a zinc containing, three-domain phosphoprotein that either exists as a hypophosphorylated (56-kDa, p56) or hyperphosphorylated species (58-kDa, p58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with NS5A HCV inhibitory activity. WO2006/133326 discloses stilbene derivatives while WO 2008/021927 and WO 2008/021928 disclose biphenyl derivatives having NS5A HCV inhibitory activity. WO 2008/048589 discloses 4-(phenylethynyl)-1H-pyrazole derivatives and their antiviral use. WO-2010/065668 discloses 5-(phenylethynyl)-1H-imidazoles and their antiviral activity.

There is a need for HCV inhibitors that may overcome the disadvantages of current HCV therapy such as side effects, limited efficacy, the emerging of resistance, and compliance failures, as well as improve the sustained viral load response.

The present invention concerns a group of HCV inhibiting phenylethynyl derivatives with useful properties regarding one or more of the following parameters: antiviral efficacy, favorable profile of resistance development, reduced or lack of toxicity and genotoxicity, favorable pharmacokinetics and pharmacodynamics, ease of formulation and administration and limited or lack of drug-drug interactions with other drugs, in particular other anti-HCV agents.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides compounds, which can be represented by the formula I-a

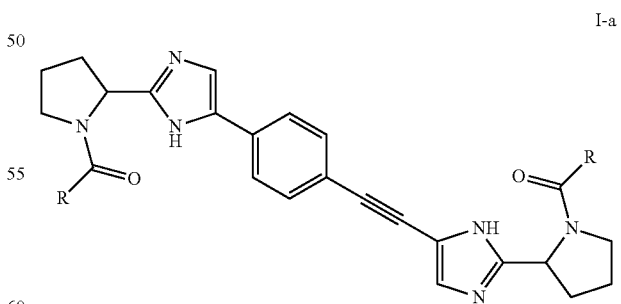

including any possible stereoisomers thereof, wherein:
R is —$CR_1R_2R_3$, alkylamino, benzylamino, arylamino, aryl optionally substituted with 1 or 2 substituents selected from halo and methyl, hetero$C_{4-7}$cycloalkyl;
$R_1$ is selected from $C_{1-4}$alkyl; phenyl optionally substituted with 1, 2 or 3 substituents independently selected from halo, $C_{1-4}$alkyl, $C_{1-4}$alkoxy, trifluoromethoxy or 2 substituents on adjacent ring atoms form a 1,3-dioxolane group; benzyl optionally substituted with halo or methoxy; phenylsulphonylmethyl; heteroaryl; heteroarylmethyl; and $C_{3-6}$cycloalkyl;

$R_2$ is selected from hydrogen, hydroxyl, amino, mono- and di-$C_{1-4}$alkylamino, $C_{1-4}$alkylcarbonylamino, $C_{1-4}$alkyloxycarbonylamino, $C_{1-4}$alkylamino-carbonylamino, piperidin-1-yl or imidazol-1-yl;

$R_3$ is hydrogen, or alternatively, $R_2$ and $R_3$ together form an oxo group or a cyclopropyl;

or a pharmaceutically acceptable salt and/or solvate thereof.

In a further aspect, the invention concerns the use of compounds of formula I, as specified herein, for inhibiting HCV. Alternatively, there is provided the use for the manufacture of a medicament of a compound of formula I or any subgroup thereof, as specified herein.

A first embodiment of the present invention concerns a compound of formula I

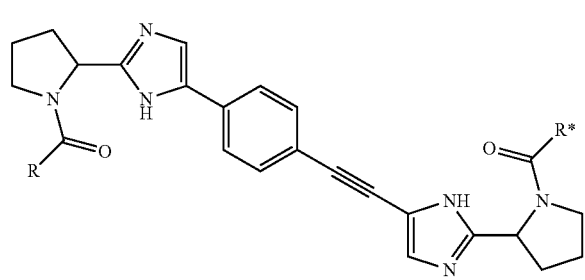

I or a stereoisomer thereof, wherein:

R and R* are each independently —$CR_1R_2R_3$, $C_{1-4}$alkylamino, benzylamino, arylamino, aryl optionally substituted with 1 or 2 substituents selected from halo and methyl, hetero$C_{3-6}$cycloalkyl; wherein $R_1$ is selected from $C_{1-4}$alkyl; phenyl optionally substituted with 1, 2 or 3 substituents independently selected from halo, $C_{1-4}$alkyl, $C_{1-4}$alkoxy, trifluoromethoxy or 2 substituents on adjacent ring atoms form a 1,3-dioxolane group; benzyl optionally substituted with halo or methoxy; phenylsulfonylmethyl; heteroaryl; heteroarylmethyl; and $C_{3-6}$cycloalkyl;

$R_2$ is selected from hydrogen, hydroxyl, amino, mono- and di-$C_{1-4}$alkylamino, $C_{1-4}$alkylcarbonylamino, $C_{1-4}$alkyloxycarbonylamino, $C_{1-4}$alkylamino-carbonylamino, piperidin-1-yl or imidazol-1-yl; and $R_3$ is hydrogen, or $R_2$ and $R_3$ together form an oxo group; or $R_1$ and $R_3$ together form cyclopropyl;

provided that when either one of R or R* represents —CH($C_6H_5$)N($CH_3$)$_2$ then the other cannot be —CH($C_6H_5$)NHC(=O)OCH$_3$; and when R and R* are identical, then $R_1$ is other than phenyl when $R_2$ is hydroxyl, acetylamino, methoxycarbonylamino or tert. butoxycarbonylamino and $R_3$ is hydrogen; and $R_1$ is other than $C_{1-4}$alkyl when $R_2$ is $C_{1-4}$alkyloxycarbonylamino and $R_3$ is hydrogen;

or a pharmaceutically acceptable salt or a solvate thereof.

Subgroups of compounds of formula I are those compounds of formula I, or subgroups of compounds of formula I, as defined herein, wherein R and R* are —$CR_1R_2R_3$ or benzylamino; in particular, wherein R and R* are —$CR_1R_2R_3$.

Subgroups of compounds of formula I are those compounds of formula I, or subgroups of compounds of formula I, as defined herein, wherein $R_2$ is hydrogen, hydroxyl, dimethylamino, acetylamino, methoxycarbonylamino, methylaminocarbonylamino, piperidin-1-yl or imidazol-1-yl.

Subgroups of compounds of formula I are those compounds of formula I, or subgroups of compounds of formula I, as defined herein, wherein $R_1$ is selected from $C_{1-4}$alkyl; phenyl optionally substituted with 1 or 2 substituents independently selected from halo, methyl, methoxy or 2 substituents on adjacent ring atoms form a 1,3-dioxolane group; heteroaryl and heteroarylmethyl. In particular, heteroaryl is pyridinyl, particularly pyridin-3-yl.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b, comprising administering to a subject in need thereof, a therapeutically effective amount of a compound as defined hereinbefore.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I have several centers of chirality. Of interest are the stereogenic centers of the pyrrolidine rings, i.e. at the 2-carbon. The configuration at this position may be that corresponding to L-proline, i.e.

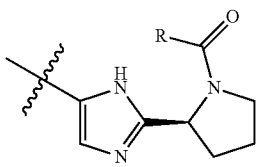

or that corresponding to D-proline, i.e.

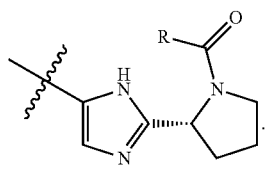

Of particular interest are compounds of formula I or subgroups of compounds of formula I, as defined herein, that are according to formula I-b

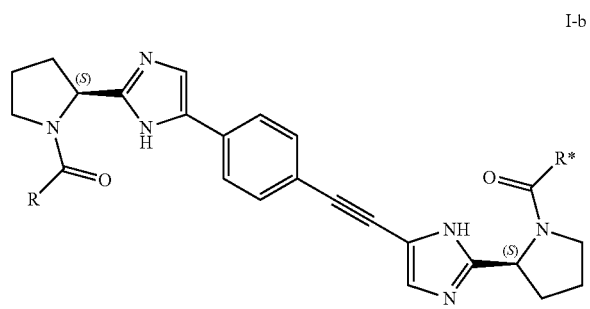

I-b

Also of interest is the configuration of the group —CR₁R₂R₃: when R₁ is selected from C₁₋₄alkyl optionally substituted with methoxy, hydroxyl or dimethylamino; C₃₋₆cycloalkyl; and tetrahydropyranyl, then the S-configuration is preferred; when R₁ is selected from phenyl optionally substituted with 1, 2 or 3 substituents independently selected from halo, C₁₋₄alkoxy, trifluoromethoxy or 2 substituents on adjacent ring atoms form a 1,3-dioxolane group; and heteroaryl; then the R-configuration is preferred.

The pharmaceutically acceptable addition salts comprise the therapeutically active non-toxic acid and base addition salt forms of the compounds of formula (I) or subgroups thereof. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form. One compound of formula I may—depending on the number of basic functionalities present in its structure—form a salt with one, two or more acid molecules.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

As used herein, "C₁₋₄alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. For the purpose of the present invention, of interest amongst C₁₋₄alkyl is C₃₋₄alkyl, i.e. straight or branched chain hydrocarbon groups having 3 or 4 carbon atoms such as 1-propyl, 2-propyl, 1-butyl, 2-butyl, 2-methyl-1-propyl, 2-methyl-2-propyl. Of particular interest may be branched C₃₋₄alkyl such as 2-propyl, 2-butyl, 2-methyl-1-propyl, 2-methyl-2-propyl.

The term "C₃₋₆cycloalkyl" as a group or part thereof, defines saturated cyclic hydrocarbon groups having from 3 to 6 carbon atoms that together form a cyclic structure. Examples of C₃₋₆cycloalkyl include cyclopropyl, cyclobutyl, cyclopentyl and cyclohexyl.

"C₁₋₄alkoxy" as a group or part of a group means a group of formula —O—C₁₋₄alkyl wherein C₁₋₄alkyl is as defined above. Examples of C₁₋₄alkoxy are methoxy, ethoxy, n-propoxy, or isopropoxy.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

As used herein for the purpose of defining "aryl" as a group or part thereof means an aromatic ring structure optionally comprising one or two heteroatoms selected from N, O and S, in particular from N and O. Said aromatic ring structure may have 5 or 6 ring atoms. Examples are phenyl, pyridinyl, oxazolyl and the like.

As used herein, the prefix "hetero-" means that the group comprises or further includes at least 1 heteroatom selected from N, O and S, in particular N and O. For example, the term "heteroaryl" means an aromatic ring structure as defined for the term "aryl" comprising at least 1 heteroatom selected from N, O and S, in particular from N and O, for example imidazolyl, furanyl, pyridinyl, oxazolyl and the like. Alternatively, the term "heteroC₄₋₇cycloalkyl" means saturated cyclic hydrocarbon group as defined for "C₃₋₆cycloalkyl" further comprising at least 1 heteroatom selected from N, O and S, in particular from N and O, for example tetrahydrofuranyl, tetrahydropyranyl, pyrrolidinyl, piperidinyl, morpholinyl, piperazinyl and the like.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

Whenever used herein, the term "compounds of formula I", or "the present compounds" or similar terms, it is meant to include the compounds of formula I, including the possible stereoisomeric forms, and the pharmaceutically acceptable salts and solvates thereof.

General Synthetic Methods

The compounds of the invention wherein R and R* are identical may be obtained by acylation of the phenylethynyl scaffold of formula III with the appropriate acid of formula R—C(=O)—OH wherein R has the meaning as defined for the compounds of formula I or any subgroup thereof.

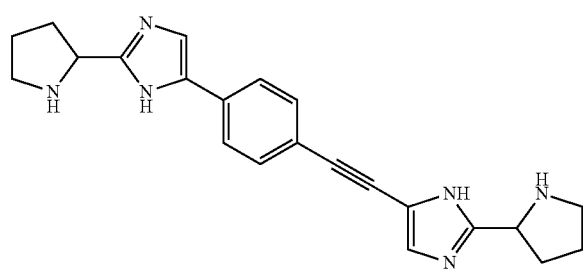

III

Said acylation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions for amino-group acylation or amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[3-(dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, or 4-DMAP. Further coupling agents are (benzotriazol-1-yloxy)-tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetramethyluronium tetrafluoroborate (TBTU), or O-(7-azabenzotriazol-1-yl)-N,N,N',N'-tetramethyluronium hexafluorophosphate (HATU). These coupling reactions can be performed in either solution (liquid phase) or solid phase.

For the purpose of the present invention, a preferred method for acylation is performed employing HATU.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

The phenylethynyl scaffold of formula III may be obtained according to the synthetic pathway illustrated by example 1 disclosed herein. Intermediate I-9 is a compound of formula III having the (S,S) configuration at the pyrrolidine moieties. Alternative compounds of formula III wherein the configuration at the pyrrolidine moieties is not (S,S) may be obtained using the same synthetic route using N-Boc-Proline of a different configuration in the synthesis of intermediate I-11.

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to act in a prophylactic way against HCV infection, to stabilize or to reduce HCV infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and hepatocellular carcinoma. A number of the compounds of this invention moreover are known to be active against mutated strains of HCV. Additionally, compounds of this invention may have attractive properties in terms of bioavailability, show a favorable pharmacokinetic profile, including an acceptable half-life, AUC (area under the curve) and peak and trough values, and lack unfavorable phenomena such as insufficiently rapid onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I, as specified herein, are useful in the inhibition of HCV replication, in particular in the treatment of warm-blooded animals, in particular humans, infected with HCV, and for the prophylaxis of HCV infections. The present invention furthermore relates to a method of treating a warm-blooded animal, in particular human, infected by HCV, or being at risk of infection by HCV, said method comprising the administration of an anti-HCV effective amount of a compound of formula I, as specified herein.

The compounds of formula I, as specified herein, may therefore be used as a medicine, in particular as an anti HCV medicine. Said use as a medicine or method of treatment comprises the systemic administration to HCV infected subjects or to subjects susceptible to HCV infection of an amount effective to combat the conditions associated with HCV infection.

The present invention also relates to the use of the present compounds in the manufacture of a medicament for the treatment or the prevention of HCV infection.

Furthermore, compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

In general it is contemplated that an antiviral effective daily amount would be from about 0.01 to about 50 mg/kg, or about 0.02 to about 30 mg/kg body weight. It may be appropriate to administer the required dose as two, three, four or more sub-doses at appropriate intervals throughout the day. Said sub-doses may be formulated as unit dosage forms, for example, containing about 1 to about 1000 mg, or about 1 to about 500 mg, or about 1 to about 100 mg, or about 2 to about 50 mg of active ingredient per unit dosage form.

Combination Therapy

The invention also relates to a combination of a compound of formula I, a pharmaceutically acceptable salt or solvate thereof, and another antiviral compound, in particular another anti-HCV compound. The term "combination" relates to a product containing (a) a compound of formula I, as defined hereinbefore, and (b) another anti-HCV inhibitor, as a combined preparation for simultaneous, separate or sequential use in the treatment of HCV infections.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other anti-HCV agent, e.g. IFN-α, pegylated IFN-α, ribavirin, albuferon, taribavirin, nitazoxanide Debio025 or a combination thereof.

Other agents that may be combined with the compounds of the present invention include, for example, nucleoside and non-nucleoside inhibitors of the HCV polymerase, protease inhibitors, helicase inhibitors, NS4B inhibitors and agents that functionally inhibit the internal ribosomal entry site (IRES) and other agents that inhibit HCV cell attachment or virus entry, HCV RNA translation, HCV RNA transcription, replication or HCV maturation, assembly or virus release. Specific compounds in these classes include HCV protease inhibitors such as telaprevir (VX-950), boceprevir (SCH-503034), narlaprevir (SCH-900518), ITMN-191 (R-7227), TMC435350 (TMC435), MK-7009, BI-201335, BI-2061 (ciluprevir), BMS-650032, ACH-1625, ACH-1095, GS 9256, VX-985, IDX-375 (HCV NS4A protease co-factor inhibitor), VX-500, VX-813, PHX-1766, PHX2054, IDX-136, IDX-316, ABT-450, EP-013420 (and congeners) and VBY-376; the nucleoside HCV polymerase inhibitors useful in the invention include R7128, PSI-7851, PSI 7977, IDX-189, IDX-184, IDX-102, R1479, UNX-08189, PSI-6130, PSI-938 and PSI-879 and various other nucleoside and nucleotide analogs and HCV inhibitors including those derived as 2'-C-methyl modified nucleosides, 4'-aza modified nucleosides, and 7'-deaza modified nucleosides, e.g. 4-amino-1-[5-azido-4-hydroxy-5-hydroxymethyl-3-methyltetrahydrofuran-2-yl]-pyrimidin-2(1H)-one (Ref 1) and the bis-2-methylpropanoate ester thereof (Ref 2). Non-nucleoside HCV polymerase inhibitors useful in the invention include HCV-796, HCV-371, VCH-759, VCH-916, VCH-222, ANA-598, MK-3281, ABT-333, ABT-072, PF-00868554, BI-207127, GS-9190, A-837093, JKT-109, GL-59728, GL-60667, ABT-072, AZD-2795 and 13-cyclohexyl-3-methoxy-17,23-dimethyl-7H-10,6-(methanoiminothioiminoethanooxyethanoiminomethano)indolo[2,1-a][2]benzazepine-14,24-dione 16,16-dioxide (Ref 3).

The following examples are meant to illustrate the invention and should not be construed as a limitation of its scope.

EXAMPLES

Example 1

Synthesis of the Phenylethynyl Scaffold of Formula III

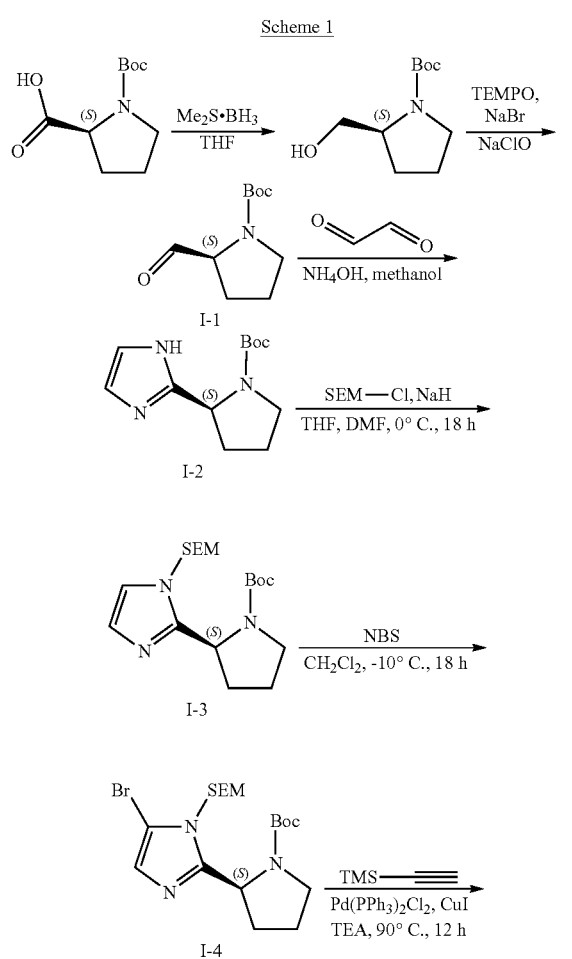

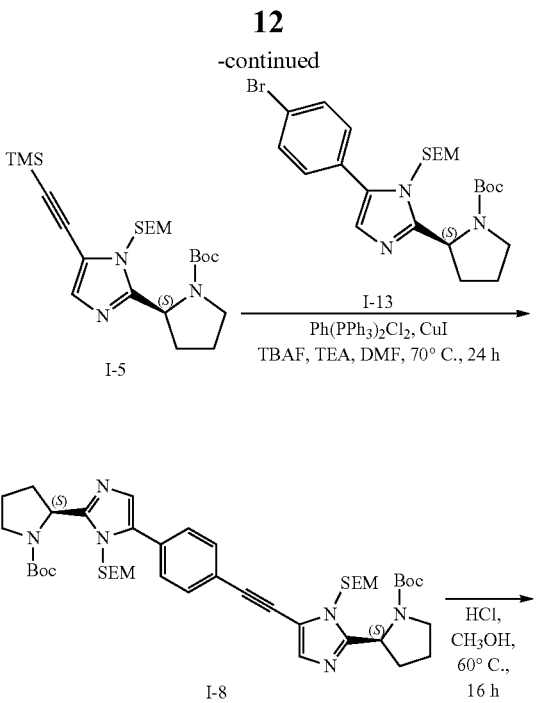

1.1 Preparation of L-Boc-prolinol

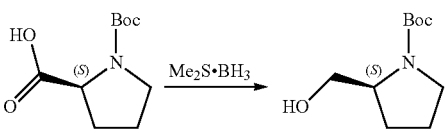

Borane-methyl sulfide complex (180 mL, 1.80 mol) was added dropwise to a solution of N-Boc-L-Proline (300 g, 1.39 mol) in anhydrous THF (3.0 L) which was cooled to 0° C. When gas evolution ceased, the ice bath was removed and the solution was stirred at 10° C. for 18 hours. Thin layer chromatography (TLC) showed that no starting material remained and that the desired product was formed. The solution was cooled to 0° C. and methanol (2.4 L) was slowly added. The solvents were removed under reduced pressure. The residue was reconstituted in dichloromethane (1 L), washed with NaHCO$_3$ (500 mL, saturated, aqueous) and brine (500 mL), dried over MgSO$_4$. The solids were removed via filtration, and the solvents of the filtrate were removed under reduced pressure to afford a white solid, 260 g (93%), used in the next step without further purification.

1.2 Preparation of L-boc-prolinal, I-1

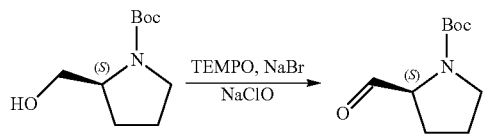

To a solution of L-Boc-prolinol (100 g, 500 mmol) in CH$_2$Cl$_2$ (1.5 L) at 0° C. were added successively, under vigorous stirring, 2,2,6,6-tetramethylpiperidine-1-oxyl (TEMPO; 1.56 g, 10 mmol) and NaBr (5.14 g, 50 mmol). To the resulting mixture was added dropwise a solution of NaHCO$_3$ (6 g, 110 mmol, dissolved in 1.5 L 6% NaClO solution) and 6% NaClO in active chlorine (1.5 L, 750 mmol) at 0° C. over a period of 1 hour. TLC showed no starting material remained and that the desired product was formed. The mixture was rapidly extracted with dichloromethane (2×1.5 L). The organic layers were combined, washed with NaHSO$_4$ (10%, 1 L) and KI (4%, 200 mL), then with Na$_2$S$_2$O$_3$ (10%, 1 L) and brine (1.5 L), dried over MgSO$_4$, the solids were removed via filration, and the solvents were removed under reduced pressure to afford a yellow oil, Boc-prolinal, I-1 (89 g, 92%), used in the next step without further purification.

1.3 Preparation of Intermediate I-2

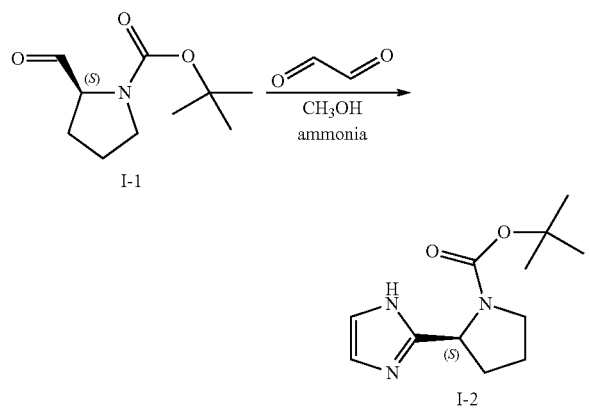

Aqueous ammonia (25~28%, 200 mL) was added dropwise to a solution of intermediate I-1 (89 g, 0.44 mol) and glyoxal (183 mL of 40% in water) in 1 L of methanol. The reaction mixture was sealed and reacted at 10° C. After 16 hours, additional glyoxal (20 mL) and aqueous ammonia (20 mL) were added and reacted for an additional 6 hours. The solvents were removed under reduced pressure, and the crude was reconstituted in ethyl acetate (1.0 L), washed with water and brine, dried over MgSO$_4$, the solids were removed via filtration and the solvents were removed under reduced pressure. The crude was purified by column chromatography (silica gel, dichloromethane to methanol/dichloromethane 1:70) to obtain 73 g (70%) intermediate 1-2 as a white solid.

$^1$H NMR: MeOD 400 MHz δ 6.95 (s, 2H), 4.82-4.94 (m, 1H), 3.60-3.70 (m, 1H), 3.41-3.50 (m, 1H), 2.20-2.39 (m, 1H), 1.91-2.03 (m, 3H), 1.47 (s, 3H), 1.25 (s, 6H)

1.4 Preparation of Intermediate I-3

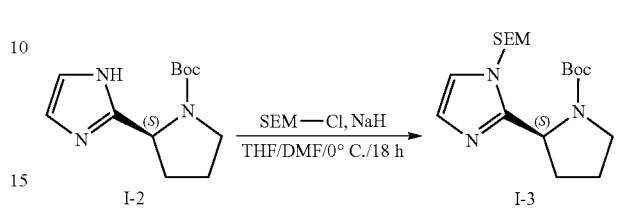

To a solution of intermediate I-2 (500 g, 2.1 mol) in anhydrous THF (1.8 L) and dimethylformamide (DMF; 0.8 L) was added sodium hydride (55 g, a 60% dispersion in oil, 2.3 mol) in portions with stirring at 0° C. over a period of 4 hours. [2-(trimethylsilyl)ethoxy]methyl (SEM) chloride (245.8 g, 2.3 mol) was added dropwise at 0° C. The resulting mixture was stirred at 25° C. for 14 hours. The reaction was quenched with water (100 mL). Then the solvent was removed under reduced pressure and the residue was dissolved in ethyl acetate (2.5 L), washed with water (2 L), brine (2 L) and dried over MgSO$_4$, the solids were removed by filtration and the solvents of the filtrate were removed under reduced pressure. The residue was purified by silica gel chromatography (petroleum ether/ethyl acetate 4:1) to obtain an oil, 530 g (68%) intermediate I-3.

1.5 Preparation of Intermediate I-4

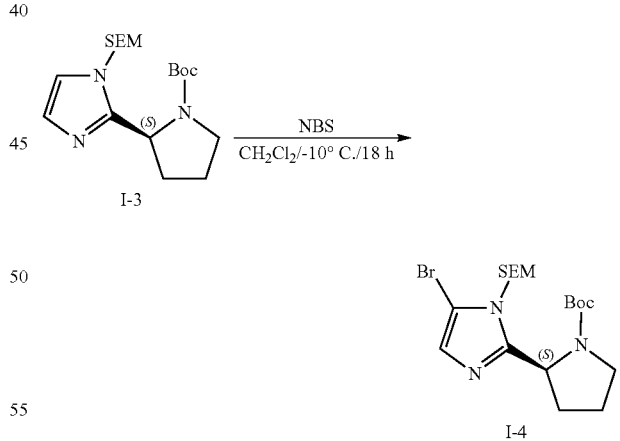

To a solution of intermediate I-3 (530 g, 1.44 mol) in dichloromethane (2 L) was added N-bromosuccinimide (NBS; 256 g, 1.44 mol) in portions with stirring at −10° C. over a period of 4 hours. The mixture was stirred for 14 hours at 20° C. The reaction mixture was washed with water (2 L), brine (2 L) and dried over MgSO$_4$, the solids were removed via filtration and the solvents of the filtrate were removed under reduced pressure. The residue was purified by chromatography (silica gel, petroleum ether/ethyl acetate 10:1). The best fractions were pooled and the solvents removed under reduced pressure to afford a yellow oil, 460 g (71%) intermediate I-4.

1.6 Preparation of Intermediate I-5

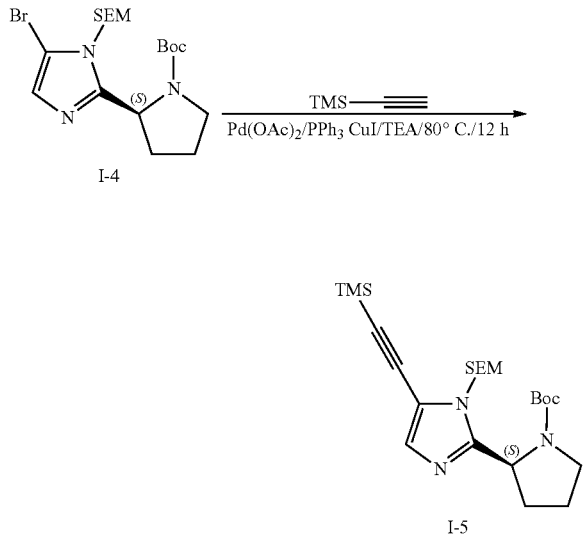

The mixture of intermediate I-4 (272 g, 609.2 mmol), trimethylsilylacetylene (TMS-acetylene; 77.8 g, 792 mmol), Pd(OAc)$_2$ (13.7 g, 60.9 mmol) and triphenylphosphine (Ph$_3$P; 31.9 g, 121.8 mmol) in triethylamine (TEA, 2 L) was stirred at 80° C. for 18 hours under N$_2$. Then TMS-acetylene (41.7 g, 426.3 mmol) was added after cooling to 20° C. The resulting mixture was then stirred at 80° C. for 8 hours under N$_2$. Next, the reaction mixture was filtered through diatomaceous earth, and the solvents of the filtrate were removed under reduced pressure. The residue was purified by chromatography on silica gel (petroleum ether/ethyl acetate 30:1 to 10:1) twice to obtain 98 g (34.7%) of intermediate I-5 as a brown solid.

$^1$H NMR: CDCl$_3$ 400 MHz δ 6.87 (s, 1H), 5.16-5.65 (m, 1H), 4.61-4.87 (m, 2H), 3.24-3.42 (m, 4H), 1.64-2.21 (m, 4H), 1.02-1.17 (d, 9H), 0.59-0.73 (m, 2H), 0.01 (s, 9H), −0.35 (s, 9H).

1.7 Preparation of Intermediate I-8

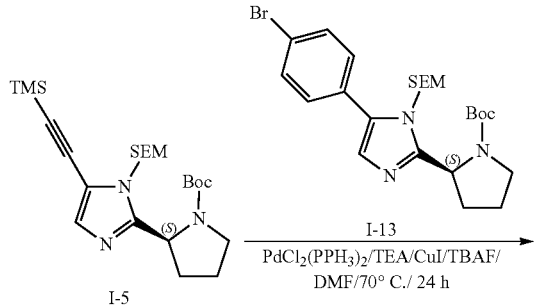

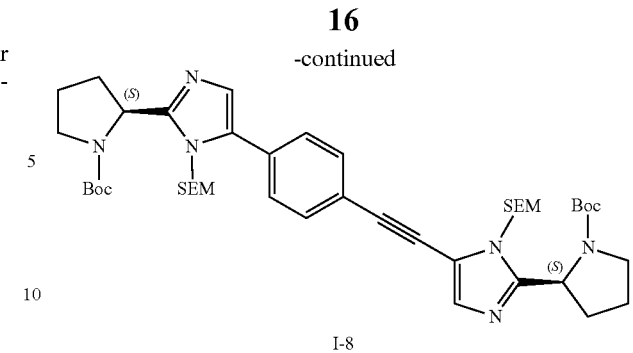

Intermediate I-5 (55 g, 118.6 mmol), intermediate I-13 (68 g, 130.46 mmol), CuI (2.26 g, 11.86 mmol), and TEA (36 g, 355.79 mmol) were combined in DMF (500 mL), then N$_2$ was bubbled through the reaction mixture, and PdCl$_2$(Ph$_3$P)$_2$ (8.32 g, 11.86 mmol) was added under N$_2$. The mixture was warmed to 70° C. and the N$_2$ flow was continued. Tetra-n-butylammonium fluoride (TBAF; 1 M in THF, 118 mL, 118 mmol) was added via a syringe pump over 10 hours. The reaction mixture was diluted with water (1 L) and extracted with a mixture of petroleum ether and ethyl acetate (1:1 (v:v), 2×500 mL). The combined organic layers were washed with water and brine, dried over MgSO$_4$, the solids were removed by filtration, and the solvents of the filtrate were removed under reduced pressure. The residue was purified by chromatography on silica gel (petroleum ether/ethyl acetate 2:1) to obtain 35 g crude product in 80% purity, and purified again by preparative HPLC to give 19.2 g (19.4%) intermediate 1-8 as yellow solid.

H NMR: CDCl$_3$ 400 MHz δ 7.70-7.72 (d, J=8.0 Hz, 2H), 7.49-7.51 (d, J=8.0 Hz, 2H), 7.14-7.20 (m, 2H), 5.38-5.90 (m, 2H), 4.87-5.19 (m, 4H), 3.50-3.70 (m, 8H), 1.91-2.36 (m, 8H), 1.21-1.47 (m, 18H), 0.85-0.97 (m, 4H), 0.01 (s, 18H).

1.8 Preparation of I-9

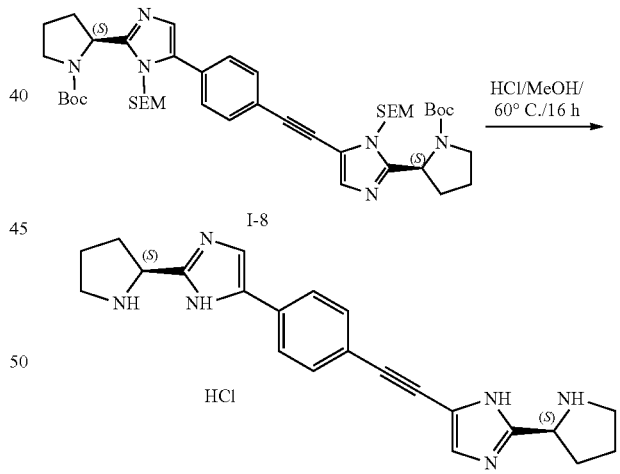

Intermediate I-9 (53.9 g, 64.6 mmol) was dissolved in methanol (250 mL), and HCl/methanol (250 mL, 4 M) was added. The mixture was stirred at 60° C. for 18 hours. 80% of the solvent was removed and acetonitrile (200 mL) was added. The resulting mixture was stirred at 60° C. for 2 hours. The resulting solid was collected by filtration and dried under vacuum to obtain 25.2 g (75.2%) solid as the hydrochloride salt.

$^1$H NMR: MeOD 400 MHz δ 7.97 (s, 1H), 7.85-7.87 (d, J=8.2 Hz, 2H), 7.66-7.68 (d, J=8.2 Hz, 2H), 7.62 (s, 1H), 4.90-5.19 (m, 2H), 3.50-3.60 (m, 4H), 2.16-2.76 (m, 8H).

1.9 Preparation of Intermediate I-11

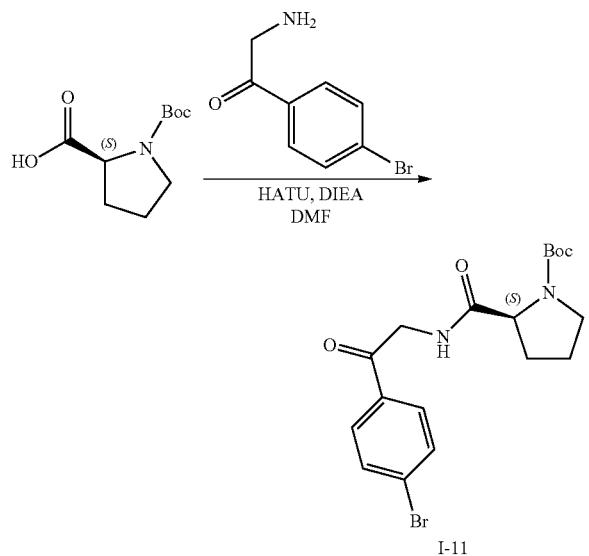

N,N-Diisopropylethylamine (80.0 g, 0.62 mol) was added dropwise, over 30 minutes, to a mixture of 2-amino-1-(4-bromo-phenyl)-ethanone (50 g, 0.2 mol), 2-(1H-7-azabenzo-triazol-1-yl)-1,1,3,3-tetramethyl uronium hexafluorophosphate methanaminium (HATU; 53 g, 0.21 mol), N-Boc-L-Proline (43.0 g, 0.2 mol) in DMF (600 mL). The reaction mixture was stirred at 5° C. for 1 hour. Most of the volatile components were removed in vacuo, and the resulting residue was partitioned between ethyl acetate (600 mL) and water (300 mL). The organic layer was washed with saturated aqueous NaHCO$_3$ (500 mL) and brine (500 mL), dried over MgSO$_4$, the solids were removed via filtration and the solvents of the filtrate were removed under reduced pressure. The crude product was purified by column chromatography (silica gel, petroleum ether/ethyl acetate 3:1 to 1:1) to obtain a pale yellow solid, 60 g (62%) of intermediate I-11.

$^1$H NMR: CDCl$_3$ 400 MHz δ 7.85 (d, J=8.4 Hz, 2H), 7.66 (d, J=8.4 Hz, 2H), 4.67-4.80 (m, 2H), 4.33-4.41 (m, 1H), 3.42-3.53 (m, 2H), 2.19-2.31 (m, 2H), 1.90-2.00 (m, 2H), 1.50 (s, 9H)

1.10 Preparation of I-12

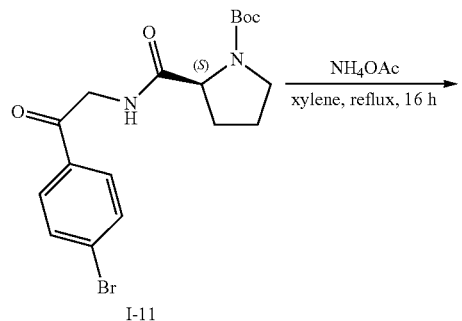

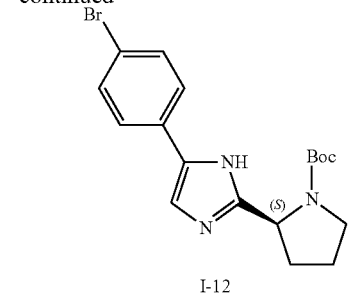

A mixture of intermediate I-11 (60 g, 0.14 mol) and ammonium acetate (89 g, 1.4 mol) in xylene (800 mL) was heated at reflux for 16 hours. The reaction mixture was partitioned between ethyl acetate (700 mL) and saturated NaHCO$_3$ solution (500 mL). The layers were separated and the aqueous layer was extracted with additional ethyl acetate (2×300 mL). The organic layers were combined, washed with brine (500 mL), dried over MgSO$_4$, the solids removed via filtration and the solvents of the filtrate were evaporated under reduced pressure. The resulting material was recrystallized from ethyl acetate/petroleum ether to afford a yellow solid, I-12, 25 g (43%).

$^1$H NMR (400 MHz, MeOD) δ ppm 1.23 (s, 6H) 1.46 (s, 3H) 1.84-2.10 (m, 3H) 2.36 (m, J=5.80 Hz, 1H) 3.50 (m, J=10.40, 5.10 Hz, 1H) 3.60-3.73 (m, 1H) 4.94-5.00 (m, 1H) 7.28-7.39 (m, 1H) 7.49 (d, J=8.28 Hz, 2H) 7.61 (d, J=8.03 Hz, 2H)

1.11 Preparation of Intermediate I-13

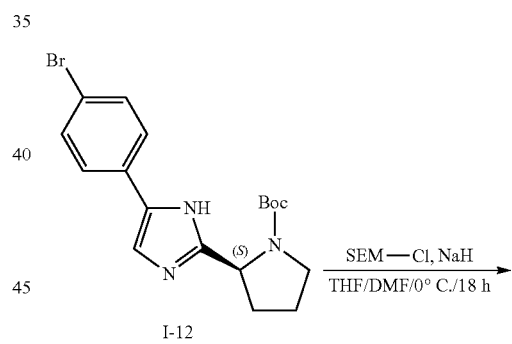

To a solution of intermediate I-12 (212 g, 540.4 mmol) in anhydrous THF (1.6 L) and DMF (0.8 L), was added sodium hydride (14.27 g, 60% dispersion in oil, 540.4 mol) in portions while stirring at 0° C. over a period of 4 hours. SEM-Cl (90.1 g, 540.4 mol) was then added dropwise at 0° C. The resulting mixture was stirred at 25° C. for 14 hours. The reaction was quenched with water (100 mL). The solvent was removed in vacuum and the residue was dissolved in ethyl acetate (2 L), washed with water, brine and dried over MgSO₄, the solids were removed by filtration, and the solvents of the filtrate were removed under reduced pressure. The residue was purified by chromatography on silica gel (petroleum ether/ethyl acetate 4:1) to obtain a yellow solid, 200 g, which was recrystallized from 1 L of petroleum ether to afford a white powder, 150 g (53.4%) intermediate I-13.

¹H NMR: DMSO 400 MHz δ 7.76 (s, 1H), 7.69-7.71 (d, J=8.4 Hz, 2H), 7.54-7.56 (d, J=8.4 Hz, 2H), 4.87-5.69 (m, 3H), 3.41-3.57 (m, 4H), 1.81-2.47 (m, 4H), 1.14-1.38 (d, 9H), 0.87-0.98 (m, 2H), 0.01 (s, 9H).

Example 2

Synthesis of Compound of Formula I 2.1 Preparation of Compound 2

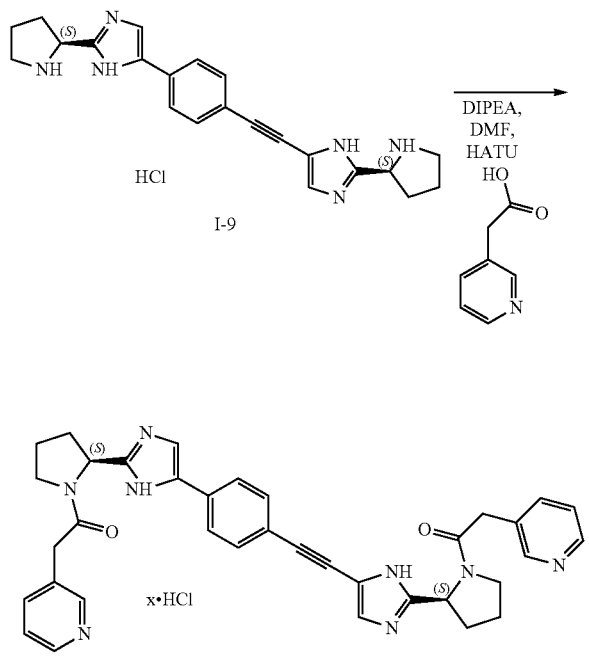

Into a 20 mL vial were placed intermediate I-9 (259 mg, 0.5 mmol), 3-pyridylacetic acid (171 mg, 1.25 mmol), HATU (475 mg, 1.25 mmol), N,N-diisopropylethylamine (DIPEA; 0.826 mL, 5 mmol) in DMF (5 mL) and the mixture was shaken 15 hours. Liquid chromatography-mass spectrometry (LCMS) showed complete conversion to the product. The solvent was removed under reduced pressure and the residue was purified using a strong cation exchanger SCX SPE column (5 g sorbent, 20 cm³). The column was treated with methanol (2 volumes), then the compound in residual DMF was loaded. Impurities were eluted with methanol (4 volumes) and then the product was released from the column by eluting with 7M ammonia in methanol (2 volumes). The solvent and excess ammonia were removed by evaporation under vacuum. Compound 2 was isolated as a yellow powder.

1H NMR (400 MHz, Chloroform-d) δ ppm 1.13 (d, J=6.44 Hz, 2H) 2.06-2.22 (m, 4H) 2.30-2.52 (m, 2H) 3.50 (s, 4H) 3.53-3.78 (m, 6H) 3.62-3.62 (m, 0H) 5.17-5.28 (m, 2H) 7.18 (s, 1H) 7.21 (s, 1H) 7.28-7.33 (m, 3H) 7.49 (d, J=7.80 Hz, 2H) 7.63 (d, J=7.61 Hz, 2H) 8.50 (d, J=1.95 Hz, 2H) 8.55 (dt, J=3.17, 1.44 Hz, 3H)

Alternatively, purification and work-up of the reaction can be carried out as followed. CH₂Cl₂ is added to the residue and the resulting solution is washed with saturated NaHCO₃. The organic phase is dried with anhydrous Na₂SO₄, filtered and concentrated in vacuo. The compound is further purified by silica gel chromatography (0-10% MeOH in CH₂Cl₂) or preparative HPLC.

Preparation of Compound 4

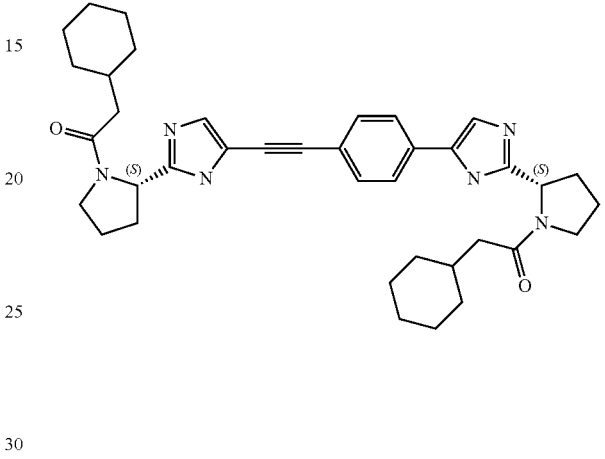

The preparation and purification of title compound 4 was performed following the procedure outlined in example 2.1 (preparation of compound 2), using 2-cyclohexyl-acetic acid in the first reaction step.

¹H NMR (400 MHz, Chloroform-d) δ ppm 0.97 (d, J=13.07 Hz, 8H) 1.09-1.21 (m, 2H) 1.22-1.37 (m, 5H) 1.69 (m, 9H) 1.83-1.93 (m, 2H) 2.01-2.12 (m, 4H) 2.15-2.43 (m, 6H) 3.49-3.61 (m, 4H) 5.11-5.34 (m, 2H) 7.12-7.24 (m, 2H) 7.36-7.56 (m, 2H) 7.65-7.81 (m, 2H)

Preparation of Compound 21

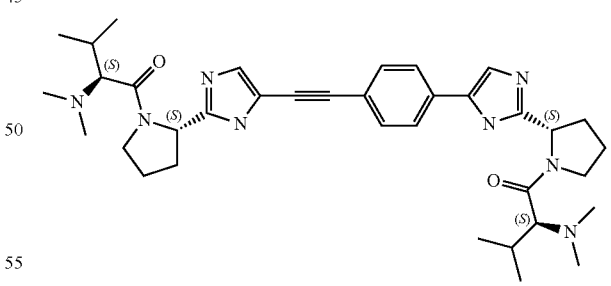

The preparation and purification of title compound 21 was performed following the procedure outlined in example 2.1 (preparation of compound 2), using (S)-2-(dimethyl-amino)-3-methylbutanoic acid in the first reaction step.

¹H NMR (400 MHz, Chloroform-d) δ ppm 0.65-0.79 (m, 5H) 1.00 (d, J=6.63 Hz, 12H) 1.99-2.23 (m, 6H) 2.42 (d, J=3.71 Hz, 12H) 2.95-3.03 (m, 2H) 3.04-3.18 (m, 1H) 3.53-

3.71 (m, 4H) 5.28-5.45 (m, 2H) 7.15-7.25 (m, 2H) 7.51 (d, J=8.39 Hz, 2H) 7.68-7.80 (m, 2H)

Preparation of Compound 28

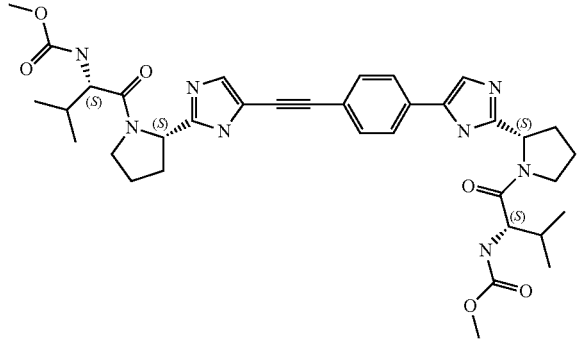

The preparation and purification of title compound 28 was performed following the procedure outlined in example 2.1 (preparation of compound 2), using (S)-2-(methoxy-carbonylamino)-3-methylbutanoic acid in the first reaction step.

$^1$H NMR (400 MHz, DMSO-$d_6$) δ ppm 0.77-0.92 (m, 4H) 1.03 (d, J=6.05 Hz, 12H) 1.19-1.30 (m, 2H) 1.83-2.05 (m, 6H) 2.06-2.22 (m, 2H) 3.53 (s, 6H) 3.56-3.65 (m, 2H) 3.68-3.87 (m, 1H) 4.04 (m, J=11.10 Hz, 1H) 4.98-5.02 (m, 1H) 5.06 (m, J=3.50 Hz, 1H) 7.28 (s, 1H) 7.30 (s, 1H) 7.42 (m, 2H) 7.50-7.59 (m, 2H) 7.71 (m, 2H)

Preparation of Compound 32

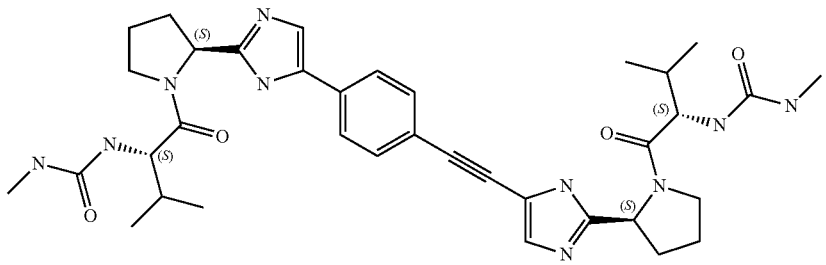

The preparation and purification of title compound 32 was performed following the procedure outlined in example 2.1 (preparation of compound 2), using (R)-2-acetamido-2-phenylacetic acid in the first reaction step.

$^1$H NMR (400 MHz, Chloroform-d) δ ppm 1.41 (br. s., 2H) 1.91 (br. s., 2H) 1.98-2.10 (m, 6H) 2.86-3.06 (m, 3H) 3.09-3.35 (m, 3H) 3.53-3.88 (m, 4H) 5.16-5.33 (m, 2H) 5.62 (d, J=6.44 Hz, 1H) 5.71-5.83 (m, 1H) 6.58-6.68 (m, 1H) 6.69-6.88 (m, 1H) 7.30 (d, J=2.54 Hz, 2H) 7.37-7.61 (m, 12H) 7.63-7.87 (m, 2H)

Preparation of Compound 36

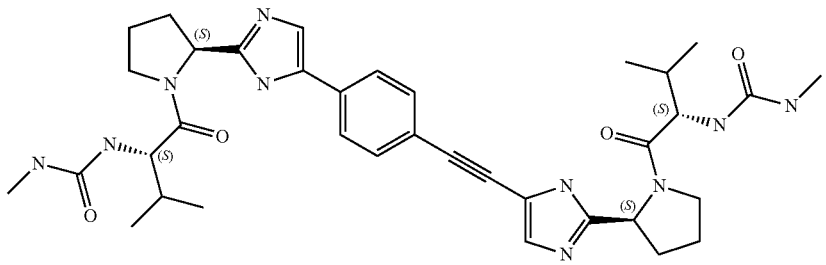

The preparation and purification of title compound 36 was performed following the procedure outlined in example 2.1 (preparation of compound 2), using (S)-3-methyl-2-(3-methylureido)butanoic acid in the first reaction step.

$^1$H NMR (400 MHz, DMSO-$d_6$) δ ppm 0.71-0.83 (m, 7H) 0.84-0.95 (m, 5H) 1.75-2.04 (m, 7H) 2.13 (br. s., 3H) 2.52-2.60 (m, 12H) 3.44 (dd, J=6.63, 3.71 Hz, 2H) 3.67-3.84 (m, 2H) 4.13-4.29 (m, 2H) 4.96-5.12 (m, 2H) 5.90 (m, J=4.70 Hz, 1H) 6.02 (d, J=8.98 Hz, 1H) 7.43 (d, J=6.24 Hz, 2H) 7.72 (d, J=7.61 Hz, 2H)

Preparation of Compound 37

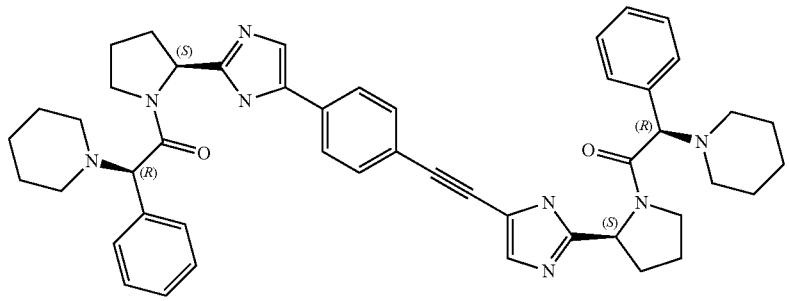

The preparation and purification of title compound 41 was performed following the procedure outlined in example 2.1 (preparation of compound 2), using (R)-2-phenyl-2-(piperidin-1-yl)acetic acid in the first reaction step.

¹H NMR (400 MHz, DMSO-d₆) δ ppm 1.04-1.56 (m, 15H) 1.70-2.03 (m, 8H) 2.10 (br. s., 2H) 2.20-2.44 (m, 9H) 3.80-4.02 (m, 1H) 4.28 (s, 2H) 4.84-5.05 (m, 1H) 6.87 (d, J=6.24 Hz, 1H) 7.14 (m, J=3.50 Hz, 2H) 7.23-7.48 (m, 10H) 7.56 (br. s., 1H) 7.76 (d, J=6.44 Hz, 2H)

2.1 Preparation of Compound 3

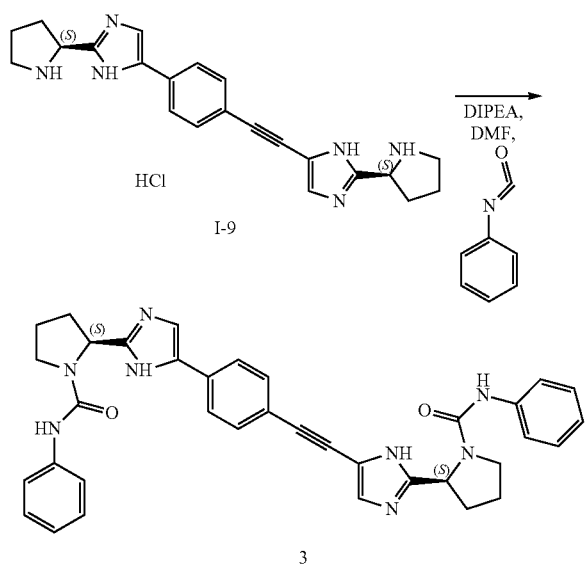

Into a 10 mL vial were placed intermediate I-9 (200 mg, 0.386 mmol), N,N-diiso-propylethylamine (0.638 mL, 3.859 mmol), phenyl isocyanate (0.126 mL, 1.158 mmol). The vial was shaken overnight at room temperature. The solvents were removed under reduced pressure, the residue was dissolved in dichloromethane (1 mL) and purified via silica gel chromatography using a dichloromethane to 10% methanol in dichloromethane gradient. The best fractions were pooled, and the solvents removed under reduced pressure to afford pure product 3.

All compounds were characterized by LC/MS. The following LC/MS methods were used:

Method A: Waters Acquity UPLC equipped with a PDA detector (range 210-400 nm) and a Waters SQD with a dual mode ion source ES+/−. The column used was a Halo C18, 2.7μ, 2.1×50 mm, and held at 50° C. A gradient of 95% aqueous formic acid (0.1%)/5% acetonitrile to 100% acetonitrile was ramped over 1.5 minutes, held for 0.6 minutes, then returned to 100% aqueous formic acid (0.1%) for 0.5 minutes. The flow rate was 0.6 mL/min.

Method B: Liquid Chromatography: Waters Alliance 2695, UV detector:Waters 996 PDA, range:210-400 nm; Mass detector: Waters ZQ, ion source: ES+, ES− Column used: SunFire C18 3.5μ 4.6×100 mm mobile phase A: 10 mM NH₄OOCH+0.1% HCOOH in H₂O; mobile phase B: CH₃OH; column temp.: 50° C.; flow: 1.5 ml/min gradient time (min) [% A/% B] 0 [65/35] to 7[5/95] to 9.6[5/95] to 9.8[65/35] to 12 [65/35].

Method C: Waters Acquity UPLC equipped with a PDA detector (range 210-400 nm) and a Waters SQD with a dual mode ion source ES+/−. The column used was a XS Strategy 1.7μ, 2.1×20 mm, and held at 50 C. A gradient of 100% aqueous formic acid (0.1%) to 100% acetonitrile was ramped over 1.5 minutes, held for 0.6 minutes, then returns to 100% aqueous formic acid (0.1%) for 0.5 minutes. The flow rate was 0.6 mL/min.

TABLE 1 compounds of formula I

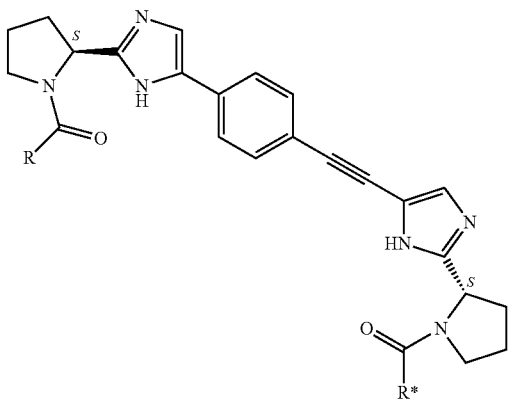

| Compound no. | R—C(=O)* = R*—C(=O)* *Denotes the attachment of the radical | Exact Mass | Observed Mass (M + H⁺) | Rt (Min.) [method] |
|---|---|---|---|---|
| 1 |  | 608.29 | 609 | 0.80 [A] |

TABLE 1-continued
compounds of formula I
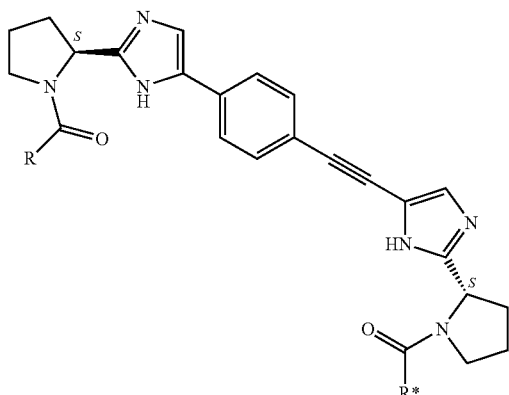
| Compound no. | R—C(=O)* = R*—C(=O)* *Denotes the attachment of the radical | Exact Mass | Observed Mass (M + H+) | Rt (Min.) [method] |
|---|---|---|---|---|
| 2 | | 610.28 | 611 | 0.48 [A] |
| 3 | | 610.28 | 611 | 0.76 [A] |
| 4 | | 620.38 | 621 | 1.00 [A] |
| 5 | | 696.27 | 697 | 0.65 [A] |
| 6 | | 636.25 | 637 | 0.87 [A] |
| 7 | | 764.25 | 765 | 0.79 [A] |
| 8 | | 568.28 | 569 | 0.62 [A] |
| 9 | | 638.31 | 639 | 0.57 [A] |

TABLE 1-continued
compounds of formula I
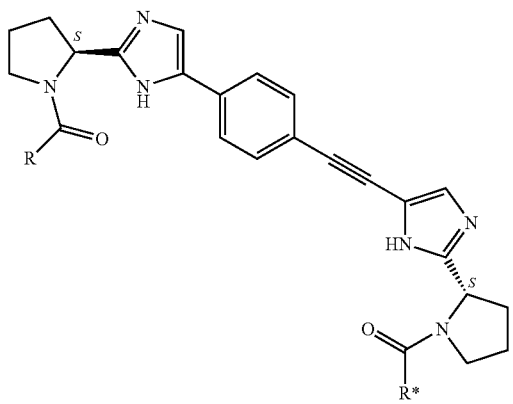
| Compound no. | R—C(=O)* = R*—C(=O)*  *Denotes the attachment of the radical | Exact Mass | Observed Mass (M + H⁺) | Rt (Min.) [method] |
|---|---|---|---|---|
| 10 | tetrahydrofuran-2-yl carbonyl | 568.28 | 569 | 0.62 [A] |
| 11 | 3-(1H-imidazol-4-yl)propanoyl | 616.30 | 617 | 0.56 [A] |
| 12 | 2-(2-(trifluoromethoxy)phenyl)acetyl | 776.25 | 777 | 1.03 [A] |
| 13 | 2-(3,5-difluoro-4-methoxyphenyl)acetyl | 740.27 | 741 | 0.93 [A] |
| 14 | 3-(2-fluorophenyl)propanoyl | 672.30 | 673 | 0.95 [A] |
| 15 | 2-hydroxy-2-phenylacetyl | 640.28 | 641 | 0.75 [A] |
| 16 | 3-(3-methoxyphenyl)propanoyl | 696.34 | 697 | 0.92 [A] |

TABLE 1-continued
compounds of formula I
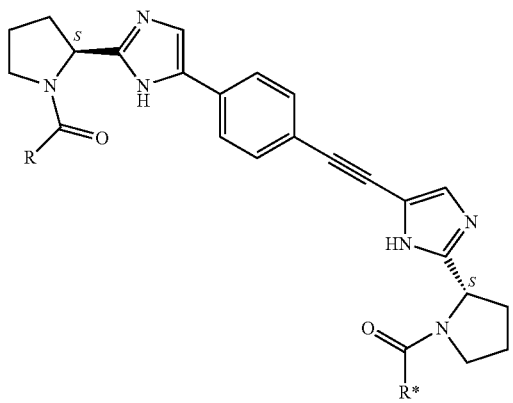
| Compound no. | R—C(=O)* = R*—C(=O)* *Denotes the attachment of the radical | Exact Mass | Observed Mass (M + H+) | Rt (Min.) [method] |
|---|---|---|---|---|
| 17 | 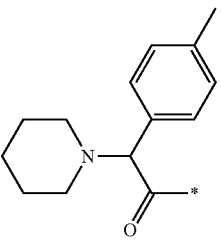 [SMILES: *C(=O)C(c1ccc(C)cc1)N1CCCCC1] | 802.47 | 803 | 0.72 [A] |
| 18 | 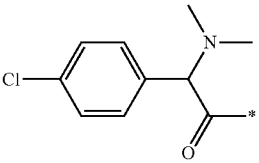 [SMILES: *C(=O)C(c1ccc(Cl)cc1)N(C)C] | 762.30 | 763 | 0.68 [A] |
| 19 | 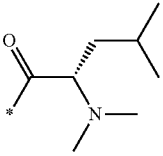 [SMILES: *C(=O)[C@H](CC(C)C)N(C)C] | 654.44 | 655 | 0.60 [A] |
| 20 | 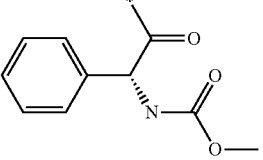 | 754.32 | 755 | 0.84 [A] |
| 21 | 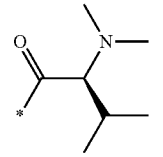 [SMILES: *C(=O)[C@H](C(C)C)N(C)C] | 626.41 | 627 | 0.57 [A] |
| 22 | 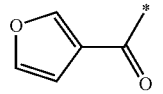 | 560.22 | 561 | 0.69 [A] |

TABLE 1-continued
compounds of formula I
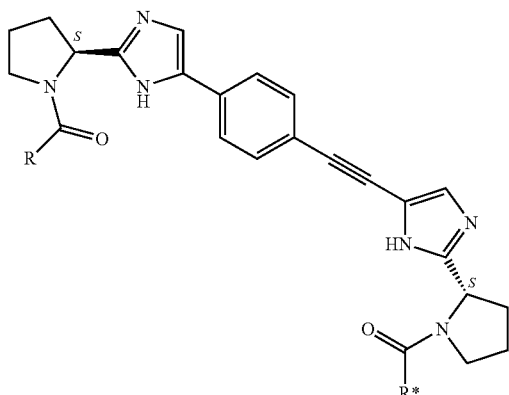
| Compound no. | R—C(=O)* = R*—C(=O)* *Denotes the attachment of the radical | Exact Mass | Observed Mass (M + H+) | Rt (Min.) [method] |
|---|---|---|---|---|
| 23 | 2-pyridyl-C(=O)* | 582.25 | 583 | 0.67 [A] |
| 24 | 3-pyridyl-C(=O)* | 582.25 | 583 | 0.61 [A] |
| 25 | 4-F-phenyl-C(=O)* | 616.24 | 617 | 0.83 [A] |
| 26 | phenyl(imidazol-1-yl)CH-C(=O)* | 740.33 | 741 | 0.62 [A] |
| 27 | 2,5-dimethyloxazol-4-yl-C(=O)* | 618.27 | 619 | 0.74 [A] |
| 28 | MeO-C(=O)-NH-CH(iPr)-C(=O)* | 686.35 | 687 | 0.76 [A] |
| 29 | iPr-NH-C(=O)* | 542.31 | 543 | 0.62 [A] |
| 30 | PhCH2-NH-C(=O)* | 638.31 | 639 | 0.79 [A] |

TABLE 1-continued
compounds of formula I
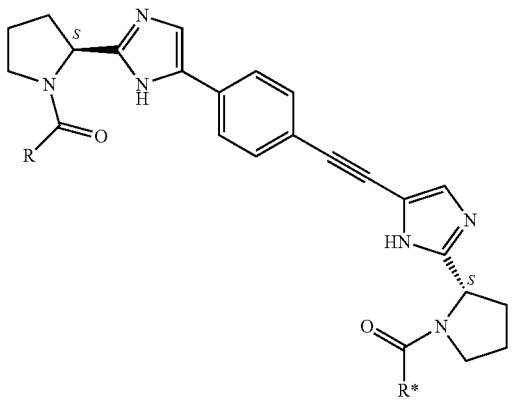
| Compound no. | R—C(=O)* = R*—C(=O)* *Denotes the attachment of the radical | Exact Mass | Observed Mass (M + H⁺) | Rt (Min.) [method] |
|---|---|---|---|---|
| 31 | 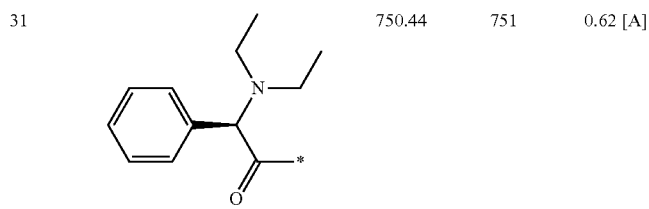 | 750.44 | 751 | 0.62 [A] |
| 32 | 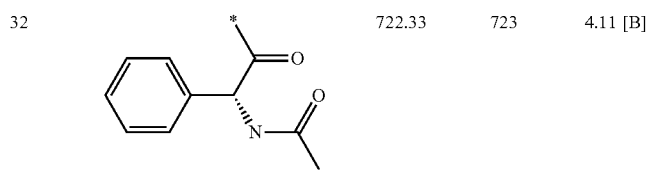 | 722.33 | 723 | 4.11 [B] |
| 33 | 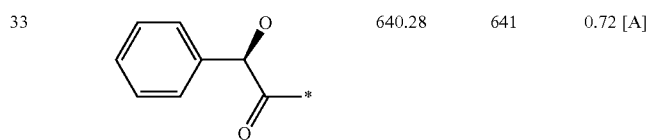 | 640.28 | 641 | 0.72 [A] |
| 34 | 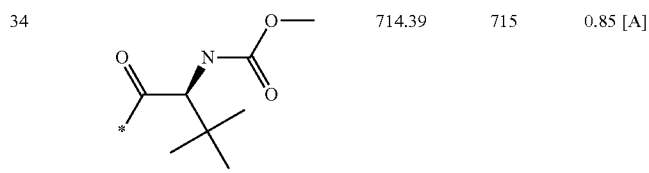 | 714.39 | 715 | 0.85 [A] |
| 35 | 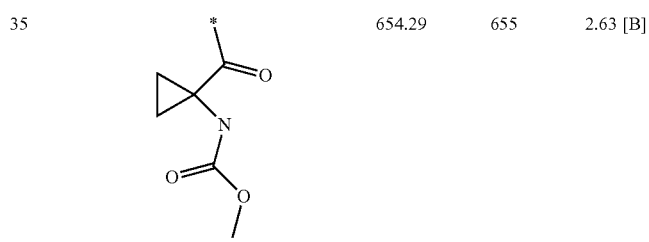 | 654.29 | 655 | 2.63 [B] |

TABLE 1-continued compounds of formula I

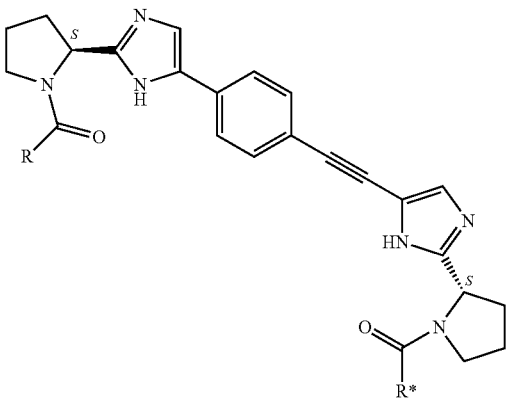

| Compound no. | R—C(=O)* = R*—C(=O)* *Denotes the attachment of the radical | Exact Mass | Observed Mass (M + H⁺) | Rt (Min.) [method] |
|---|---|---|---|---|
| 36 | ![structure] | 684.39 | 685 | 3.62 [B] |
| 37 | ![structure] | 775.01 | 776 | 1.85 [B] |
| 38 | ![structure] | 686.81 | 689 | 0.60 [A] |
| 39 | ![structure] | 630.70 | 631 | 0.52 [A] |
| 40 | ![structure] | 658.76 | 659 | 0.55 [A] |

Example 3

Biological Activity of the Compounds of Formula I

Replicon Assay

The compounds of formula (I) were examined for inhibitory activity in the HCV replicon. This cellular assay is based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows:

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is flanked by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which represent the amount of compound required to decrease the level of detected luciferase activity by 50%, or more specifically, to reduce the ability of the genetically linked HCV replicon RNA to replicate.

Table 2 shows the replicon results obtained for compounds of the examples given above.

TABLE 2

| Compound no. | R—C(=O)— = R*—C(=O)— | $EC_{50}$ (μM) |
|---|---|---|
| 1 | phenylacetyl | 0.00026 |
| 2 | (pyridin-3-yl)acetyl | 0.0015 |
| 3 | phenylaminocarbonyl | 0.81 |
| 4 | cyclohexylacetyl | 0.13 |
| 5 | (benzo[d][1,3]dioxol-5-yl)acetyl | 0.0048 |
| 6 | 2-oxo-2-phenylacetyl | 0.018 |
| 7 | 3-(phenylsulfonyl)propanoyl | 0.057 |
| 8 | (S)-tetrahydrofuran-2-carbonyl | 0.56 |
| 9 | 3-(pyridin-3-yl)propanoyl | <0.00048 |
| 10 | (R)-tetrahydrofuran-2-carbonyl | 0.018 |
| 11 | 3-(1H-imidazol-4-yl)propanoyl | 0.25 |

TABLE 2-continued
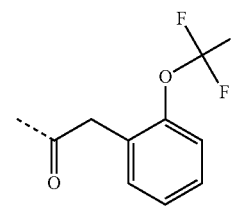
| Compound no. | R—C(=O)— = R*—C(=O)— | EC$_{50}$ (μM) |
|---|---|---|
| 12 | 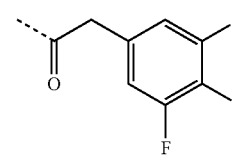 | 0.29 |
| 13 | 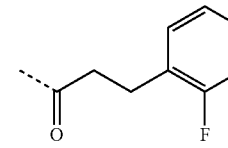 | 0.76 |
| 14 | 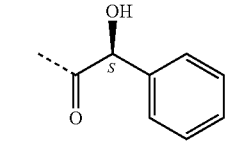 | 0.093 |
| 15 | 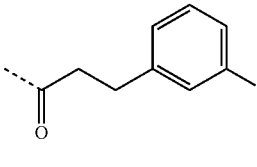 | 0.00069 |
| 16 | 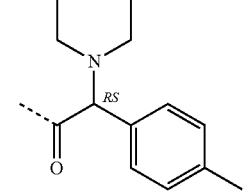 | 1.03 |
| 17 | 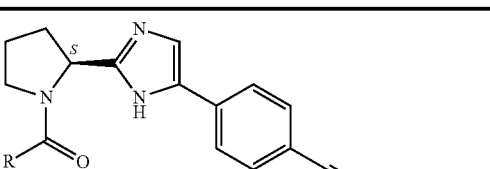 | 0.00011 |
TABLE 2-continued
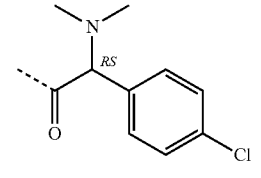
| Compound no. | R—C(=O)— = R*—C(=O)— | EC$_{50}$ (μM) |
|---|---|---|
| 18 | 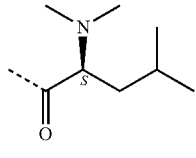 | 0.000091 |
| 19 | 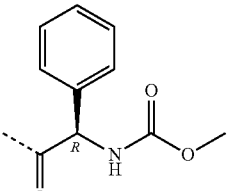 | 0.11 |
| 20 | 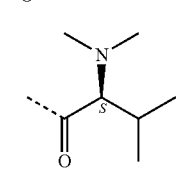 | 0.000020 |
| 21 | 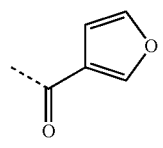 | 0.036 |
| 22 | 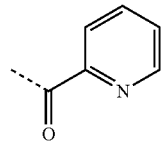 | 0.031 |
| 23 | 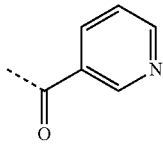 | 3.95 |
| 24 | 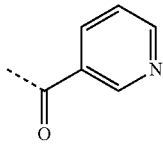 | 1.0058 |

TABLE 2-continued

| Compound no. | R—C(=O)— = R*—C(=O)— | EC$_{50}$ (μM) |
|---|---|---|
| 25 | 4-fluorobenzoyl | 1.023 |
| 26 | 2-(1H-imidazol-1-yl)-2-phenylacetyl (RS) | 0.00095 |
| 27 | 2,5-dimethyloxazole-4-carbonyl | 0.018 |
| 28 | (S)-2-((methoxycarbonyl)amino)-3-methylbutanoyl | 0.000036 |
| 29 | N-isopropylcarbamoyl | 0.28 |
| 30 | N-benzylcarbamoyl | 0.00077 |
| 31 | (R)-2-(diethylamino)-2-phenylacetyl | 0.00026 |
| 32 | (R)-2-acetamido-2-phenylacetyl | <0.00048 |
| 33 | (R)-2-hydroxy-2-phenylacetyl | 0.00022 |
| 34 | (S)-2-((methoxycarbonyl)amino)-3,3-dimethylbutanoyl | 0.00008 |
| 35 | 1-((methoxycarbonyl)amino)cyclopropanecarbonyl | 0.068 |
| 36 | (S)-3-methyl-2-(3-methylureido)butanoyl | 0.00069 |
| 37 | (R)-2-phenyl-2-(piperidin-1-yl)acetyl | 0.00003 |

TABLE 2-continued

| Compound no. | R—C(=O)— = R*—C(=O)— | EC$_{50}$ (μM) |
|---|---|---|
| 38 | | 0.0054 |
| 39 | | >0.98 |
| 40 | | 0.00023 |

The invention claimed is:

1. A compound of formula I:

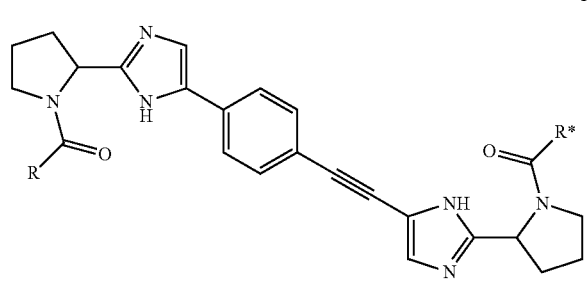

I or a stereoisomer thereof, wherein:

R and R* are each independently —CR$_1$R$_2$R$_3$, C$_{1-4}$alkylamino, benzylamino, arylamino, aryl optionally substituted with 1 or 2 substituents selected from halo and methyl, hetero C$_{4-7}$cycloalkyl; wherein R$_1$ is selected from C$_{1-4}$alkyl; phenyl optionally substituted with 1, 2 or 3 substituents independently selected from halo, C$_{1-4}$alkyl, C$_{1-4}$alkoxy, trifluoromethoxy or 2 substituents on adjacent ring atoms form a 1,3-dioxolane group; benzyl optionally substituted with halo or methoxy; phenylsulfonylmethyl; heteroaryl; heteroarylmethyl; and C$_{3-6}$cycloalkyl;

R$_2$ is selected from hydrogen, hydroxyl, amino, mono- and di-C$_{1-4}$alkylamino, C$_{1-4}$alkylcarbonylamino, C$_{1-4}$alkyloxycarbonylamino, C$_{1-4}$alkylamino-carbonylamino, piperidin-1-yl or imidazol-1-yl;

R$_3$ is hydrogen, or alternatively,

R$_2$ and R$_3$ together form an oxo group; or

R$_1$ and R$_3$ together form cyclopropyl;

provided that when either one of R or R* represents —CH(C$_6$H$_5$)N(CH$_3$)$_2$ then the other cannot be —CH(C$_6$H$_5$)NHC(=O)OCH$_3$; and when R and R* are identical, then R$_1$ is other than phenyl when R$_2$ is hydroxyl, acetylamino, methoxycarbonylamino or tert. butoxycarbonylamino and R$_3$ is hydrogen; and R$_1$ is other than C$_{1-4}$alkyl when R$_2$ is C$_{1-4}$alkylcarbonylamino and R$_3$ is hydrogen;

or a pharmaceutically acceptable salt thereof.

2. A compound according to claim 1 wherein R and R* are —CR$_1$R$_2$R$_3$ or benzylamino.

3. A compound according to claim 2 wherein R and R* are —CR$_1$R$_2$R$_3$.

4. A compound according to claim 1 wherein R$_2$ is hydrogen, hydroxyl, dimethylamino, acetylamino, methoxycarbonylamino, methylaminocarbonylamino, piperidin-1-yl or imidazol-1-yl.

5. A compound according to claim 1 wherein R$_1$ is selected from C$_{1-4}$alkyl; phenyl optionally substituted with 1 or 2 substituents independently selected from halo, methyl, methoxy or 2 substituents on adjacent ring atoms form a 1,3-dioxolane group; heteroaryl and heteroarylmethyl.

6. A compound according to claim 5 wherein said heteroaryl is pyridinyl.

7. A compound according to claim 1 wherein the compound is of formula I-b

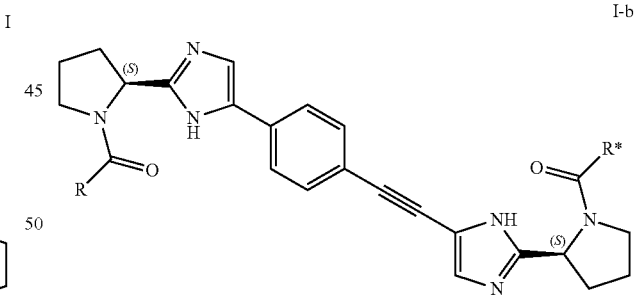

I-b

8. A pharmaceutical composition comprising a compound as defined in claim 1, and a pharmaceutically acceptable carrier.

9. A method for treating an HCV infection in a mammal comprising administering to said mammal a pharmaceutical composition according to claim 8.

* * * * *